(12) United States Patent
Bracci

(10) Patent No.: US 9,023,003 B1
(45) Date of Patent: May 5, 2015

(54) NEONATAL ABSORBENCY PAD AND RELATED METHODS

(76) Inventor: Jennifer J. Bracci, Palmetto Bay, FL (US)

(*) Notice: Subject to any disclaimer, the term of this patent is extended or adjusted under 35 U.S.C. 154(b) by 378 days.

(21) Appl. No.: 13/536,928

(22) Filed: Jun. 28, 2012

Related U.S. Application Data

(63) Continuation-in-part of application No. 12/898,835, filed on Oct. 6, 2010, now Pat. No. 8,491,555.

(60) Provisional application No. 61/248,982, filed on Oct. 6, 2009.

(51) Int. Cl.
*A61B 19/00* (2006.01)
*A61F 13/15* (2006.01)
*A61F 13/45* (2006.01)

(52) U.S. Cl.
CPC ..................... *A61F 13/45* (2013.01)

(58) Field of Classification Search
CPC .............. A61F 13/493; A61F 13/505; A61F 13/00021; A61F 13/00063; A61F 2013/15154; A61F 2013/008; A61F 2013/00812; A61F 5/48; A61F 5/485
USPC .............. 604/356, 385.01, 385.05, 385.11, 604/385.14; 428/43
See application file for complete search history.

(56) References Cited

U.S. PATENT DOCUMENTS

| | | | |
|---|---|---|---|
| 2,699,779 A * | 1/1955 | Lustig | 604/307 |
| 3,761,973 A * | 10/1973 | Leventhal | 5/484 |
| 4,045,833 A | 9/1977 | Mesek et al. | |
| 4,097,943 A | 7/1978 | O'Connell | |
| 4,627,426 A | 12/1986 | Wegener et al. | |
| 5,148,558 A | 9/1992 | Dunn | |
| 5,252,374 A | 10/1993 | Larsonneur | |
| 5,662,636 A | 9/1997 | Benjamin et al. | |
| 5,792,088 A | 8/1998 | Felder et al. | |
| 5,839,648 A * | 11/1998 | Brigand et al. | 229/87.05 |
| 5,998,694 A * | 12/1999 | Jensen et al. | 602/57 |
| 6,720,006 B2 * | 4/2004 | Hanke et al. | 424/484 |
| 7,340,842 B2 | 3/2008 | Rabe | |
| 2004/0039363 A1 | 2/2004 | Sugiyama et al. | |
| 2005/0204471 A1 | 9/2005 | Ruiz | |
| 2007/0003603 A1 | 1/2007 | Karandikar et al. | |
| 2007/0056096 A1 | 3/2007 | Assink | |
| 2009/0183309 A1 * | 7/2009 | Stinson | 5/81.1 T |

FOREIGN PATENT DOCUMENTS

WO WO 2008079060 A1 * 7/2008

* cited by examiner

*Primary Examiner* — Tan-Uyen (Jackie) T Ho
*Assistant Examiner* — Kathryn E Ditmer
(74) *Attorney, Agent, or Firm* — Allen Dyer Doppelt Milbrath & Gilchrist

(57) ABSTRACT

The invention is directed to a planar pad manufactured from three layers, each layer made from materials of differing properties. A contact layer being safe for a neonatal infant's skin is the top layer. The middle layer is an absorption layer positioned immediately below the contact layer. The absorption layer is of a two-part construction having a first half and a corresponding second half which abuts the first half. The absorption layer is operable for dispersing and containing fluids within the pad. The bottom layer is a waterproof barrier layer which is posited directly below the absorbency layer, preferably constructed of flashspun high-density polyethylene, and is also a two part construction. An internal pull tab maintains the pad in a single assembly. Upon removing the pull tab, the pad assembly splits into two separate assembly halves.

11 Claims, 7 Drawing Sheets

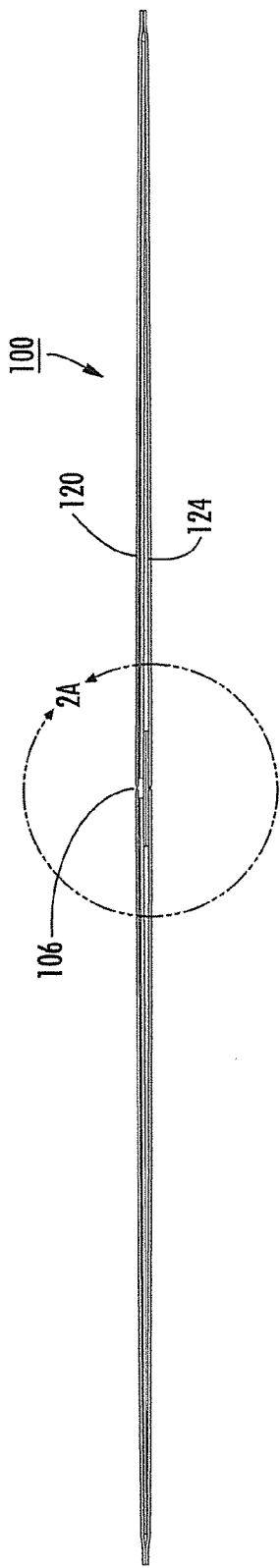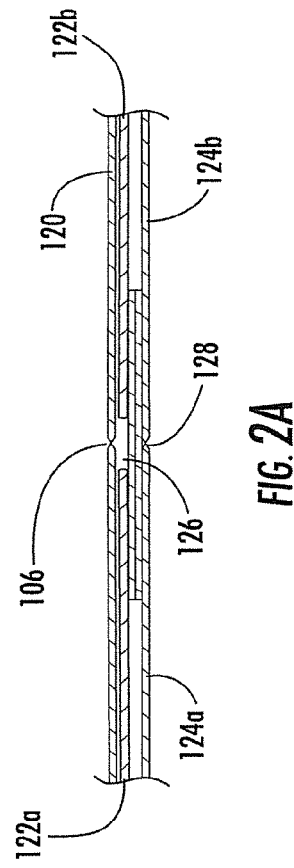

NEONATAL ABSORBENCY PAD AND RELATED METHODS

CROSS-REFERENCE TO RELATED APPLICATION

This application is a continuation in part of U.S. patent application Ser. No. 12/898,835 filed on Oct. 6, 2010 entitled "Absorbency Pad for Use in Neonatal Care and Related Method of Use," the contents of which are incorporated by reference herein, and claims priority to U.S. Provisional Patent Application Ser. No. 61/248,982 filed on Oct. 6, 2009 entitled "Perforated Absorbency Pad for Use in Neonatal Care," the contents of which are incorporated by reference herein.

FIELD OF THE INVENTION

This invention is directed toward an absorbency pad for use with low birth weight or unstable infants incubated in a neonatal intensive care unit that reduces the amount of contact with the infant and a related method of use.

BACKGROUND OF THE INVENTION

Premature birth, also commonly known as preterm birth, occurs when the infant is born after less than 37 weeks of gestation. Statistically, premature infants are at a greater risk of short- and long-term complications, including impediments in growth and mental development. Long term health effects resulting from preterm birth can include cerebral palsy, blindness, lung disease, and learning disabilities. While the underlying cause of preterm birth is generally unknown, many factors appear to be associated with premature birth, making reduction of this health risk challenging.

In most developed countries and in Europe, the preterm birth rate is generally between 5 to 9 percent. However, in the United States, the rate has risen to an alarming 12 to 13 percent over the last several decades. In fact from 1990 to 2005, premature births in this country have risen over 20 percent. This translates to roughly 500,000 preterm births each year.

There are several classifications of preterm birth, based largely upon the gestational age and birth weight. A low birth weight infant (LBW) refers to any infant weighing less than 5 pounds, 8 ounces. A very low birth weight infant ("VLBW") includes an infant born less than 3 pounds, 5 ounces. Finally, an extremely low birth weight infant ("ELBW") is an infant who weighs less than 2 pounds, 2 ounces. Each year, approximately 40,000 ELBW infants are born in the United States.

Most hospitals in developed countries maintain neonatal intensive care units ("NICUs") capable of treating preterm infants, as well as low birth weight infants (including VLBW and ELBW infants) or any infant requiring hospital intervention. Highly trained and specialized nurses who are capable of treating neonatal infants staff these NICUs. Most NICUs keep neonatal infants in specialized incubators that create a confined and isolated environment to provide regulated temperature and proper life support and respiratory systems.

When treating neonatal infants, especially VLBW and ELBW infants, most NICUs attempt to reduce or even eliminate physical contact as much as possible for the first 72 hours after birth (once these infants are placed into an incubator or onto a radiant warmer and connected to life support, respiratory systems and monitors). This is because these neonatal infants have extremely fragile skin, high sensitivity to touch, and are at a larger risk of intraventricular hemorrhaging (a rupturing of the capillaries in the brain, which can be caused in part in handling low birth weight infants).

Due to these risks, doctors and nurses try to adhere to a minimal stimulation protocol by clustering care, for example, to allow babies longer periods of rest. Currently, however, there is no simple or safe way to change neonatal bed linens. Instead, it is simply common practice to place an absorbent cotton blanket in the incubator (or on the radiant warmer) prior to treating the neonatal infant. Once a blanket becomes soiled with blood, urine, feces or materials used to treat the neonatal infant (i.e., betadine or saline), they are removed from the incubator or radiant warmer. This typically occurs through briefly lifting the neonatal infant, removing the soiled blanket and positioning a new and clean blanket (requiring multiple staff assisting in this process).

There are multiple drawbacks with this current system commonly used in NICUs. First, the brief relocation of the neonatal infant to remove the soiled blankets can cause trauma, bruising or even possible intraventricular hemorrhaging. Second, repositioning the neonate to remove the soiled blanket risks extubation of endotracheal tubes required for ventilation, which can cause damage, injury or even death to the neonate—or at the very least severe discomfort. Finally, even with removal of the top layered blanket, there is a risk that some secretion of fluid may seep onto the underlying incubator (or radiant warmer). Upon removal of the top cotton blanket, the neonatal infant is still exposed to this fluid, risking infection.

Accordingly, there is a need in the art of treating neonatal infants—especially those with VLBW and ELBW—or any unstable newborn within an incubator or radiant warmer to reduce the amount of physical contact with NICU personnel. Moreover, there is a need in the art to manufacture bed barriers that allow removal of soiled bed blankets without disrupting or moving the neonatal infant to reduce the risk of trauma and/or injury.

SUMMARY OF THE INVENTION

The present invention contemplates an essentially planar neonatal pad comprising a contact layer having a top side and a bottom side with a substantially medial perforation extending longitudinally to promote ease of separating the contact layer into a first panel and a second panel. The contact layer is selected from the material group comprising acrylics, high density polyethylene, low density polyethylene, polyester, polyolefins, polyurethanes, polyurethane-polyurea copolymers, rayons, spunbond polypropylene, and blends of these materials. In an alternate embodiment, the contact layer comprises material containing silver nano-particulates.

An absorbency layer is positioned to underlie the bottom side of the contact layer, and comprises a first half and a second half, the first half abutting the second half proximate the medial perforation of the contact layer to define an absorbency layer cleavage. The absorbency layer is generally coextensive with the contact layer to receive fluids passing through the contact layer, and is operable for dispersing and containing fluid within the neonatal pad. The pad is substantially rectangular in shape having an upper edge, a lower edge, a left side and corresponding right side.

The absorbency layer is selected from the material group comprising acrylics, bamboo, cellulose materials, cotton, high density polyethylene, low density polyethylene, polyester, polyolefins, polyurethanes, polyurethane-polyurea copolymers, rayons, superabsorbent polymers, wools, and blends of these materials.

A waterproof barrier layer having a top side and a bottom side is positioned to underlie the absorbency layer. The barrier layer comprises a first half and a second half, the first half abutting the second half proximate the absorbency layer cleavage to define a barrier layer cleavage that is generally coextensive with the contact layer. The absorbency layer is sandwiched between the contact layer and the waterproof barrier layer.

The waterproof barrier layer is selected from the material group comprising acrylics, spun bound high density polyethylene, high density polyethylene, layered low density polyethylene film, low density polyethylene, polyester, polyolefins, polyurethanes, polyurethane-polyurea copolymers, polytetrafluoroethylene, spunbond polypropylene, and blends of these materials.

A sealing pull strip having an anchoring end and a pull tab end is removably adhered to the top side of the barrier layer along the barrier layer cleavage to maintain the first half of the barrier layer in a position adjacent to the second half of the barrier layer. The pull strip underlies the absorbency layer, wherein the pull strip is a sufficient length to traverse substantially the length of the barrier layer along the barrier layer cleavage and maintain a fold in the pull strip to double back across the length of the barrier layer. The pull tab end of the pull strip extends beyond a first edge of the barrier layer. The purpose of the pull strip is to hold the barrier layer cleavage together until the pull strip is pulled away from the barrier layer so to disengage the first half of the barrier layer from the second half of the barrier layer.

In a preferred embodiment, the contact layer is bonded to the absorbency layer, and the barrier layer is bonded to the absorbency layer.

At least one handle tab is attached to the bottom side of the barrier layer, and protrudes past a second edge of the barrier layer substantially opposite the first edge of the barrier layer, the handle tab providing a handle for a user to hold for the purpose of stabilizing the neonatal pad while the pull strip tab end is being pulled.

The invention also comprises a method of maintaining a neonatal infant, the method comprising the steps of: placing a first pad assembly onto a bed portion of a neonate incubator; adding at least one additional pad assembly under the first pad, the additional pad having an essentially similar construction as the first pad; placing a neonatal infant on the first pad assembly; determining whether the first pad assembly has become soiled by the neonatal infant; pulling a pull strip of the first pad assembly to separate the first pad assembly into a first half, a second half, and an unattached pull strip; removing the first half of the first pad assembly from the incubator without picking up the neonatal infant; removing the second half of the first pad assembly from the incubator without picking up the neonatal infant; and exposing the adjacent additional pad assembly to the neonatal infant.

A preferred embodiment includes the step of holding a handle tab to assist in stabilizing the first pad assembly while the pull strip is being pulled from the first pad assembly.

A preferred embodiment of the method of treating a neonatal infant described herein specifically includes the utilization of the neonatal pad described above.

BRIEF DESCRIPTION OF THE DRAWINGS

For a fuller understanding of the invention, reference is made to the following detailed description, taken in connection with the accompanying drawings illustrating various embodiments of the present invention, in which:

FIG. 2 is a schematic illustration of a side cutaway view of the invention illustrated in FIG. 1;

FIG. 2A is a close-up schematic illustration of a side cutaway view of the indicated region of FIG. 2.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternate embodiments.

The Pad Assembly

Figure 1:
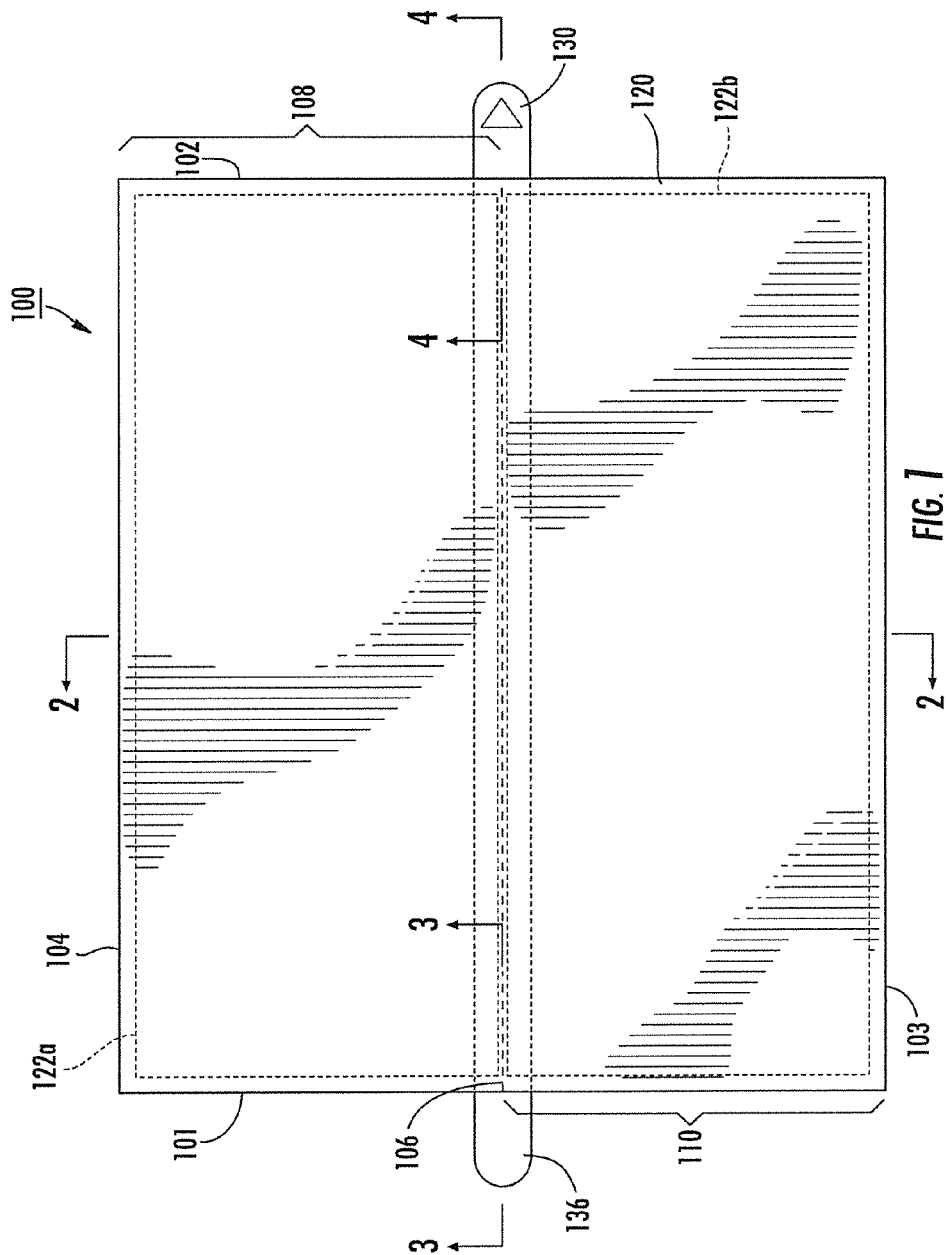
FIG. 1 is a schematic illustration of a top view of a preferred embodiment of the invention.

Referring initially to FIG. 1, the invention is directed to a pad assembly 100. Referring next to FIG. 2 and FIG. 2A, the pad assembly 100 comprises a plurality of layers including a contact layer 120, a first absorption layer panel 122a, a second absorption layer panel 122b (collectively referred to as the absorption layer 122), and a barrier layer 124. As shown in FIG. 1, the pad 100 is essentially rectangular and includes an upper edge 101, a lower edge 102, a left side edge 103, and a right side edge 104. Moreover, the pad 100 is of a sufficient size and dimension to be placed and maintained within a NICU incubator.

As further illustrated in FIG. 1, located approximately in the middle of the pad assembly 100 is a perforation 106 capable of being separated that, upon separation, divides the contact layer 120 into a first panel 108 and a second panel 110. The perforation 106 extends from the upper edge 101 to the lower edge 102. By pulling the left side edge 103 of the pad 100 apart and away from the right side edge 104, the perforation 106 allows the first panel 108 to detach from the second portion 110.

Referring to FIG. 1, and to FIG. 1 of U.S. patent application Ser. No. 12/898,835, in one embodiment, the pad assembly 100 includes a depiction of a ruler or similar measuring device located on the contact layer 120. Such ruler preferably includes a wetness indicator. Once a neonatal infant (N) (FIG. 6) is placed onto the pad 100, her height is measured through use of the ruler without moving or disturbing the infant (N), thus reducing risk of trauma and/or injury to the infant (N). In one embodiment, the pad assembly 100 comprises a thermo-indicator that allows detection of a fever and/or sudden change in body temperature. For example, should the neonatal infant (N) maintain a temperature above average, a thermo-chemical located on the pad assembly 100 will turn a distinct color to alert medical personnel of a potential medical issue. It is contemplated that one embodiment includes areas proximate the outer edges 101, 102, 103, 104 of the contact layer 120 include regions of colored material (for example, the color green) that may be calming or soothing to the neonatal infant (N), and therefore useful for chromotherapy holistic healing and generally pleasing aesthetics. The contact layer 120 of the pad assembly 100 includes a recording area. The recording area provides a space for a medical professional to denote current medical information relating to the neonatal infant (N). Such medical information includes at least one of the patient name, date of birth, time of birth, weight, measurements (including head circumference, chest circumference, abdominal girth, length), pulse, respiratory rate, blood pressure, temperature, and location of intravenous access, and any other medically relevant information.

The Contact Layer

As illustrated in FIG. 1, FIG. 2 and FIG. 2A, the pad assembly 100 comprises a contact layer 120. The contact layer 120 is preferably positioned at the top surface of the pad assembly 100 such that it is the layer that interacts with the neonatal infant (N). Thus, the contact layer 120 must be capable of allowing a variety of bodily fluids such as urine, feces, blood and other effluvia to pass through the contact layer 120 so the bodily fluids are absorbed by the absorption layer 122. This contact layer 120 must also be resistant to degradation mediated by bodily fluids and those fluids used during medical care, such as betadine, saline, alcohols, oil-based ointments, and any other liquids found in a medical environment.

Preferably, the contact layer 120 is manufactured from a soft, smooth and non-stick material. While such layer is non-abrasive and hypoallergenic, the contact layer 120 should be designed such that is not too slippery. Several materials can be used for the contact layer 120 including both woven and non-woven materials which are at least one of natural fibers, synthetic fibers, and combinations thereof. In a preferred embodiment, the contact layer 120 is made from 0.5 ounce spunbond polypropylene, which exhibits advantageous filtration properties, high tensile strength, and excellent chemical resistance. In one embodiment, the contact layer 120 is a blend of polymer fibers which are coated with polytetrafluoroethylene (Teflon™) or a similar non-stick material. In another embodiment, interdisbursed throughout the polymer fibers are nano-silver particulates. Such nano-silver particulates help to reduce bacterial and microbial build-up on the contact layer 120 due to their bacteriostatic and antimicrobial properties. It is important to note that the addition of nano-silver particulates to the contact layer 120 does not render the pad 100 incompatible for x-ray or similar imaging procedures.

As shown in FIG. 1, the contact layer 120 includes a perforation 106 such that the contact layer can be split into two panels 108 and 110 for removal away from the neonate infant (N). The bottom side of the contact layer 120 includes an adhesive material sufficient to engage the absorption layer 122. The bottom side of the contact layer 120 includes an adhesive material sufficient to engage the barrier layer 124.

The Absorption Layer

Still referring to FIG. 2, in addition to a contact layer 110, the pad assembly 100 also preferably comprises an absorption layer 122. The absorption layer 122 is positioned to underlie the bottom side of the contact layer 120. Preferably, the length and width of the absorption layer 122 is substantially coextensive with the contact layer 120. In a preferred embodiment, both the contact layer 120 and absorption layer 122 are bonded to each other.

The absorption layer 122 is preferably made of natural fibers, woven together, capable of absorbing various fluids. Alternatively, the absorption layer 122 can be manufactured from a high absorbency synthetic material. Regardless of structure (fill or fiber, woven or non-woven), it is preferable that the natural fiber be made out of bamboo due to its high absorbency and antimicrobial properties. However, other natural fibers such as merino wool and cotton are also contemplated. The absorption layer 122 is therefore made from at least one of bamboo, cotton, wools, spandex, and polyester. The materials are in the form of terry, double loop terry, fleece, jersey, flannel, batting, thermal, weave, interlock, rib, and combinations thereof.

The absorption layer 122 is of two-part construction such that it comprises a first panel 122a and a corresponding second panel 122b. The first panel 122a abuts the second panel 122b proximate the perforation 106 of the contact layer 120. A cleavage point 126 is defined by the joint where the first half of the absorption layer 122 abuts the second half of the absorption layer 122. The cleavage point 126 is the location where the absorption layer 122 separates into two separate halves upon breaking the perforation 106 of the contact layer 120 and separating the contact layer into two panels 108, 110.

It is also contemplated that a variety of thermo-chemicals, known to those of ordinary skill in the art, be utilized in the pad assembly 100, proximate the absorption layer 122, to create warmth for a neonatal infant (N) in addition to the warmth provided by the incubator.

The absorption layer 122 and the contact layer 120 can also act as treatment vehicles by the inclusion of compounds to help treat and/or prevent injury and infection to the neonatal infant (N). These medicines can include, but are not limited to, antibacterial agents (e.g. as Benzalkonium Chloride 0.1%), antiviral agents, antifungal agents, antiparasitic agents, moisturizing agents, and any other compounds known to help treat and/or prevent injury and infection, and combinations thereof.

The Barrier Layer

Still referring to FIG. 2 and FIG. 2A, the barrier layer 124 is positioned to underlie the bottom side of the absorption layer 122. Preferably, the length and width of the barrier layer 124 is substantially coextensive with the contact layer 120. In a preferred embodiment, both the barrier layer 124 and absorption layer 122 are bonded to each other.

The barrier layer 124 is preferably made of a waterproof material such as low density polyethylene bonded to 0.8 ounce spun bond polypropylene. Alternatively, the barrier layer 124 is made from at least one of acrylics, spun bound high density polyethylene, high density polyethylene, layered low density polyethylene film, low density polyethylene, polyester, polyolefins, polyurethanes, polyurethane-polyurea copolymers, polytetrafluoroethylene, spunbond polypropylene, and blends of these materials. The barrier layer 124 prevents liquids present in the absorption layer from passing below the barrier layer 124.

The barrier layer 124 is of two-part construction such that it comprises a first barrier panel 124a and a corresponding second barrier panel 124b. The first barrier panel 124a abuts the second barrier panel 124b proximate the cleavage point 126 of the absorption layer. A barrier cleavage 128 is defined by the joint where the first half of the barrier layer 124a abuts the second half of the barrier layer 124b. The barrier cleavage 128 is the location where the barrier layer 124 significantly separates the barrier layer 124 into two separate panels 124a, 124b upon breaking the perforation 106 of the contact layer 120 and separating the contact layer into two panels 108, 110.

The Pull Strip

A sealing pull strip 130 having an anchored end 132 and a pull tab end 134, as illustrated in FIG. 1, is removably adhered to both the first barrier panel 124a and the second barrier panel 124b, along the length of the barrier cleavage 128. The pull strip 130 seals the barrier panels 124a, 124b together so that the barrier cleavage 128 is watertight, thus preventing any liquids from passing beyond the barrier layer 124. The adhesive to adhere the pull strip 130 to the barrier panels 124a, 124b is preferably a low-tack, pressure-sensitive adhesive.

Figure 3:
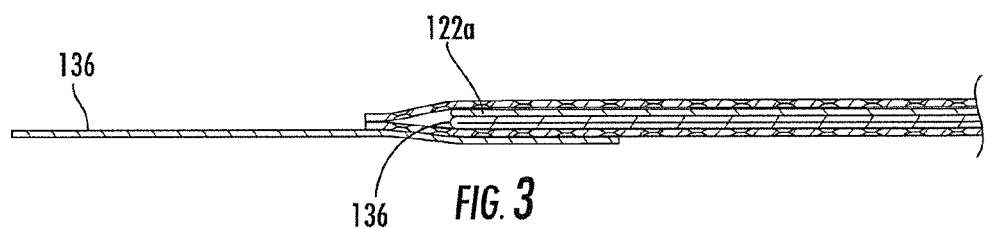
FIG. 3 is a schematic illustration of a side cutaway view of the invention illustrated in FIG. 1.
Figure 4:
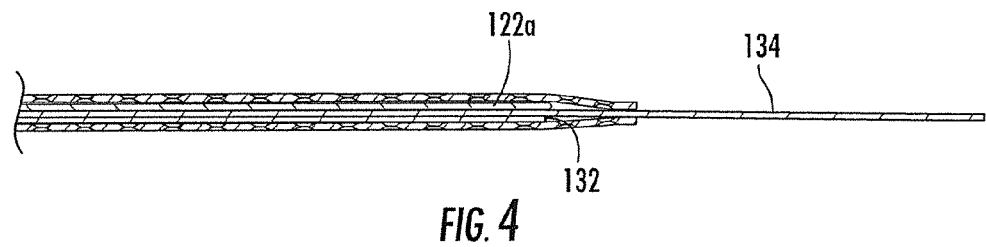
FIG. 4 is a schematic illustration of a side cutaway view of the invention illustrated in FIG. 1.

As illustrated in FIG. 1, FIG. 3, and FIG. 4, the pull strip 130 is a sufficient length to traverse the length of the barrier cleavage 128, and fold over 136 on itself and double back across the length of the pad assembly 100. The pull tab end 134 protrudes beyond the lower edge 102 of the pad assembly 100. The pull strip 130 is sandwiched above the barrier layer 124 and below the absorption layer 122. Pulling the pull tab end 134 away from the pad assembly 100 causes the pull strip 130 to release from the barrier panels 124a, 124b so that the barrier panels 124a, 124b are free to separate from each other at the barrier cleavage 128. To anchor the pad assembly 100 when pulling the pull strip 130 from the assembly 100, a handle tab 136 is attached to bottom side of the barrier layer proximate the upper edge 101 of the assembly 100.

Method of Use

Figure 5:
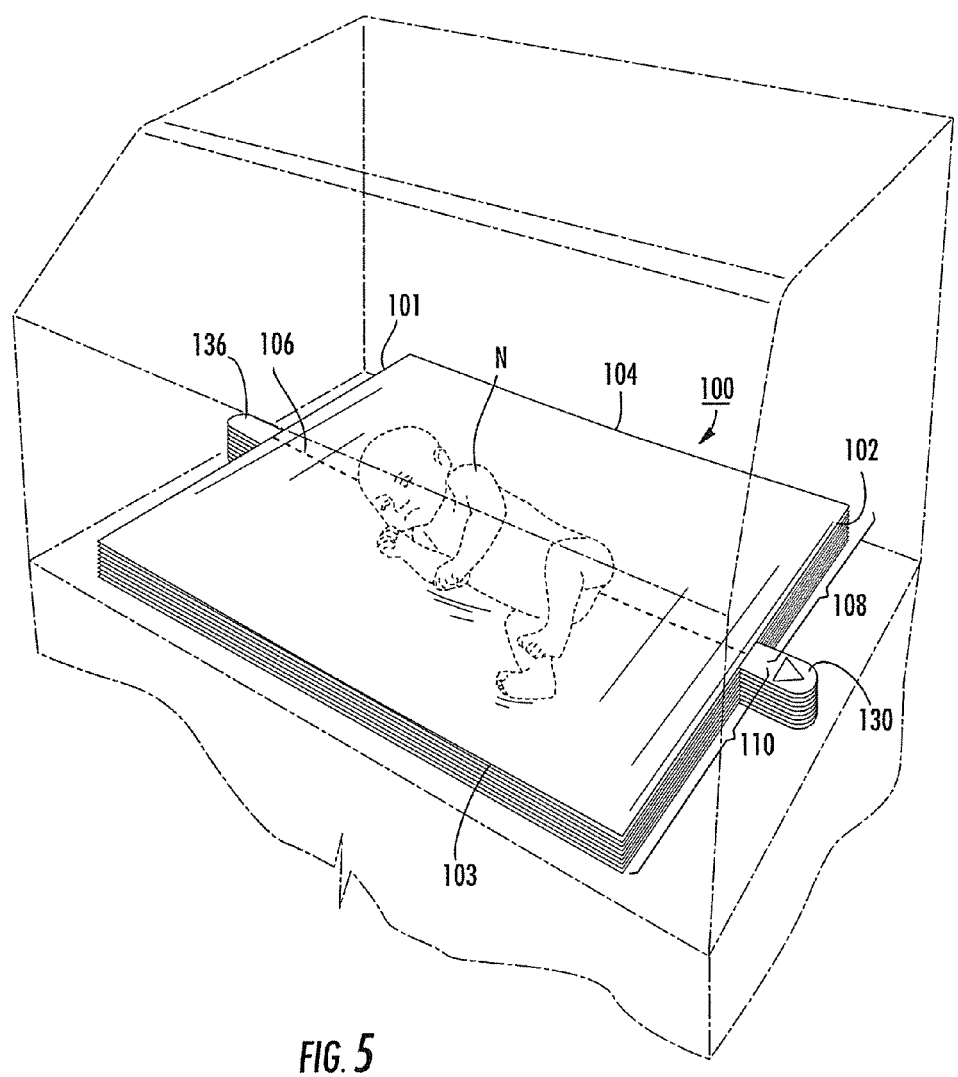
FIG. 5 is a schematic illustration of an isometric view of the invention in use inside a neonatal incubator.

As illustrated in FIG. 5, a plurality of pad assemblies 100 are stacked upon each other. These assemblies 100 are placed into a neonate incubator. This provides the bottom bedding for a neonatal infant (N). A determination is made as to whether the pad assembly 100 directly below the neonatal infant (N) is soiled by the neonatal infant (N) or from fluids used during medical care, such as betadine, saline, alcohols, oil-based ointments, and any other liquids found in a medical environment.

Figure 6:
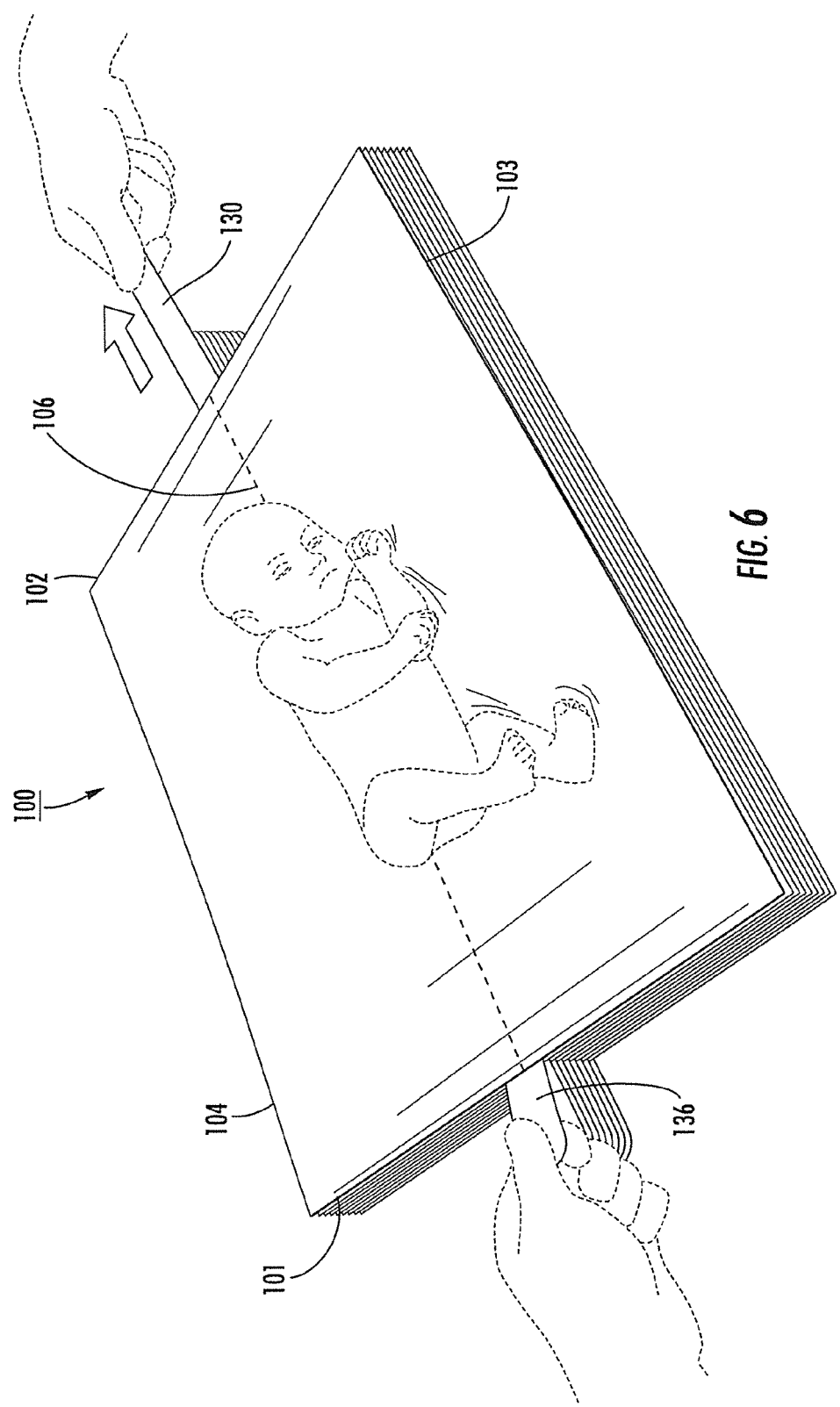
FIG. 6 is a schematic illustration of an isometric view of the invention in use.
Figure 7:
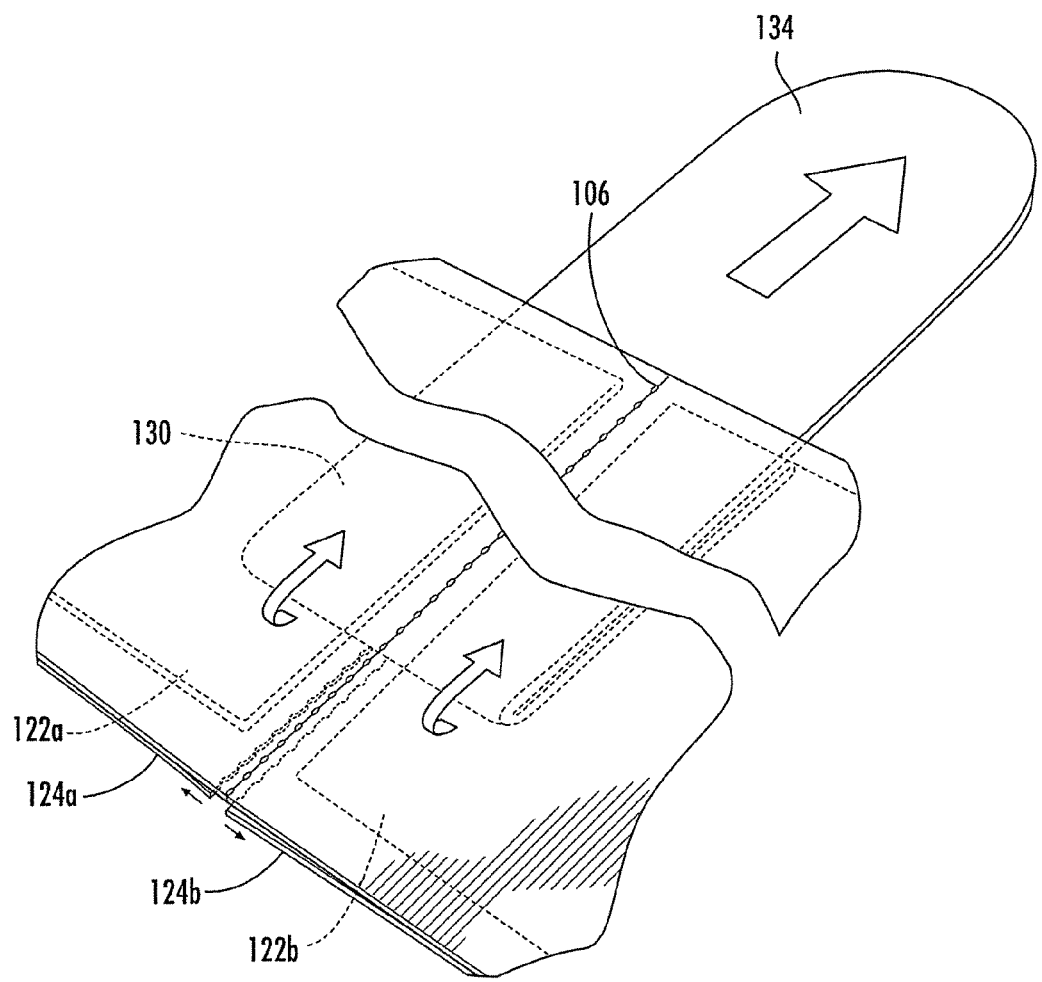
FIG. 7 is a schematic illustration of an isometric cutaway view of the pull strip being removed from the pad assembly.

FIG. 6 illustrates a person pulling the pull strip 130 from the pull tab end 134. As further illustrated by FIG. 7, pulling the pull tab end 134 away from the pad assembly 100 causes the pull strip 130 to release from the barrier panels 124a, 124b so that the barrier panels 124a, 124b are free to separate from each other at the barrier cleavage 128. The pull strip 130 is then discarded.

Figure 8:
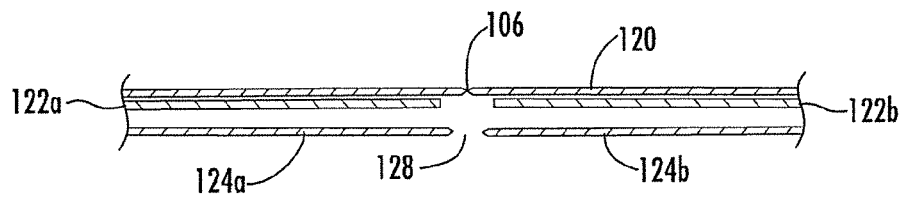
FIG. 8 is a close up schematic illustration of a side view of the pad assembly after the pull strip is removed from the pad assembly.

FIG. 8 illustrates the pad assembly 100 after the pull strip 130 has been removed from the assembly 100. The barrier cleavage 128 is made free from the pull strip 130, and the barrier panels 124a, 124b may be separated from each other. At this point the pad assembly 100 is a single assembly that is being held together solely by the perforation 106 in the contact layer 120.

Figure 9:
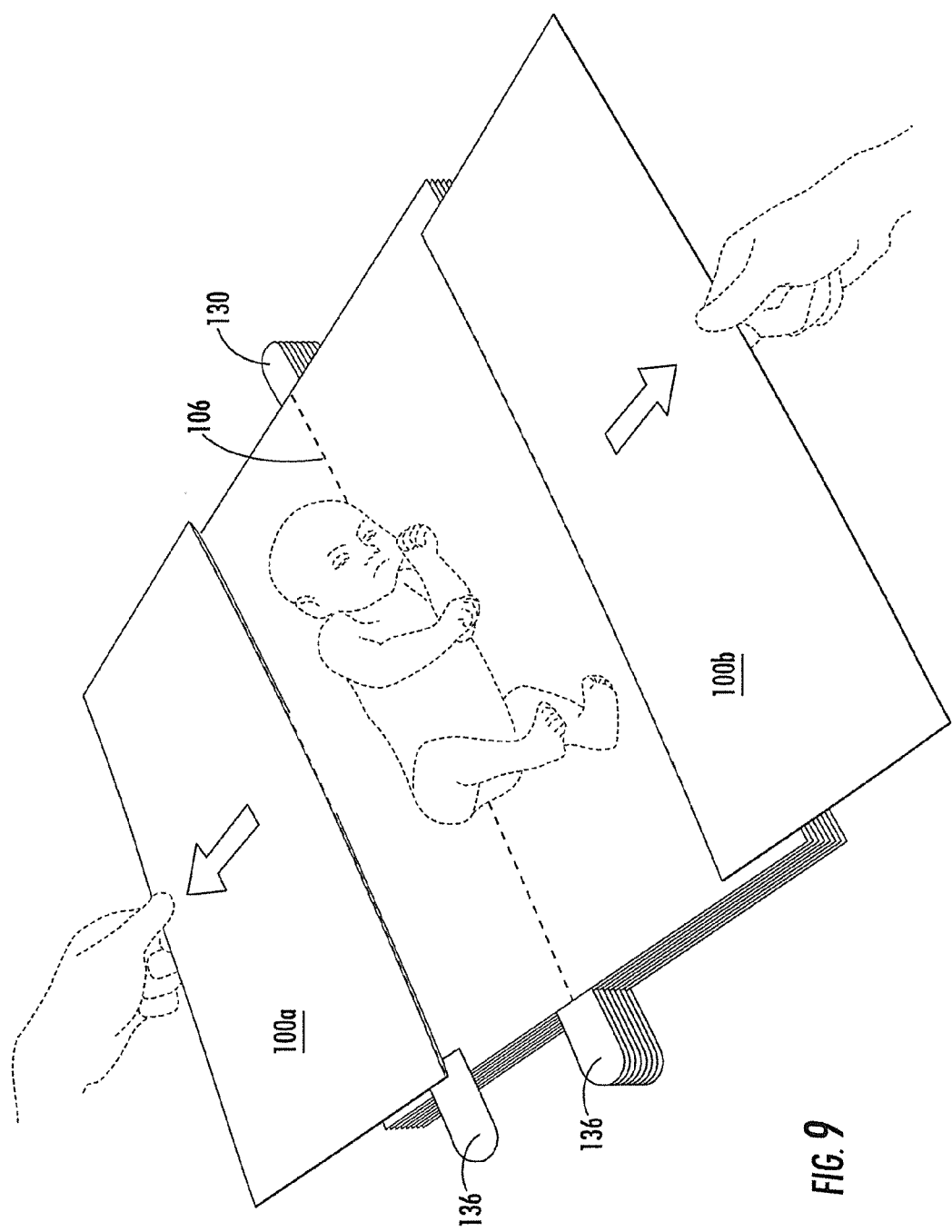
FIG. 9 is a schematic illustration of an isometric view of the invention in use.

FIG. 9 illustrates the pad assembly 100 being separated into two halves. The perforation 106 is ripped separating the pad the contact layer 120 into a first panel 108 and a second panel 110. At this point, the pad assembly 100 is three discrete pieces: a pull strip 106 that has been disengaged from the assembly 100, a first half of the pad assembly 100a and a second half of the pad assembly 100b. The first half of the pad assembly 100a and the second half of the pad assembly 100b are removed from below the neonatal infant (N), and the next clean and dry pad assembly 100 on the stack is revealed. The neonatal infant (N) need not be lifted to be exposed to clean bedding.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

The invention claimed is:

1. A neonatal pad, the pad comprising:
  a contact layer having a top side and a bottom side and a substantially medial perforation to promote ease of separating the contact layer into a first panel and a second panel;
  an absorbency layer positioned to underlie the bottom side of the contact layer, the absorbency layer comprising a first half and a second half, the first half abutting the second half proximate the medial perforation of the contact layer to define an absorbency layer cleavage, the absorbency layer being generally coextensive with the contact layer to receive fluids passing through the contact layer, the absorbency layer operable for dispersing and containing the fluid within the neonatal pad;
  a waterproof barrier layer having a top side and a bottom side, the barrier layer positioned to underlie the absorbency layer, the barrier layer comprising a first section and a second section, the first section abutting the second section proximate the absorbency layer cleavage to define a barrier layer cleavage, the barrier layer being generally coextensive with the contact layer, wherein the absorbency layer is sandwiched between the contact layer and the waterproof barrier layer; and
  a sealing pull strip having an anchoring end and a pull tab end, the pull strip being removably adhered to the top side of the barrier layer along the barrier layer cleavage to maintain the first section of the barrier layer in a position adjacent to the second section of the barrier layer, the pull strip positioned to underlie the absorbency layer, wherein the pull strip is a sufficient length to traverse substantially the length of the barrier layer along the barrier layer cleavage and maintain a fold in the pull strip to double back across the length of the barrier layer, wherein the pull tab end of the pull strip extends beyond a first edge of the barrier layer, the pull strip being for the purpose of holding the barrier layer cleavage together until the pull strip is pulled away from the barrier layer to disengage the first section of the barrier layer from the second section of the barrier layer.

2. A method of treating a neonatal infant, the method comprising the steps of:
  placing a plurality of pad assemblies onto a bed portion of a neonate incubator each of the plurality of pad assemblies having an essentially similar construction;
  placing a neonatal infant on an uppermost pad assembly of the plurality of pad assemblies;
  determining whether the uppermost pad assembly has become soiled by the neonatal infant;
  pulling a pull strip of the uppermost pad assembly to separate the uppermost pad assembly into a first half, a second half, and an unattached pull strip;
  separately removing the first and second halves of the uppermost pad assembly from the incubator without picking up the neonatal infant to expose a next uppermost pad assembly of the plurality of pad assemblies to the neonatal infant;

wherein each of the plurality of pad assemblies comprises:

a contact layer having a top side and a bottom side and a substantially medial perforation to promote ease of separating the contact layer into a first panel and a second panel;

an absorbency layer positioned to underlie the bottom side of the contact layer, the absorbency layer comprising a first half and a second half, the first half abutting the second half proximate the medial perforation of the contact layer to define an absorbency layer cleavage, the absorbency layer being generally coextensive with the contact layer to receive fluids passing through the contact layer, the absorbency layer operable for dispersing and containing the fluids;

a waterproof barrier layer having a top side and a bottom side, the barrier layer positioned to underlie the absorbency layer, the barrier layer comprising a first half and a second half, the first half abutting the second half proximate the absorbency layer cleavage to define a barrier layer cleavage, the barrier layer being generally coextensive with the contact layer, wherein the absorbency layer is sandwiched between the contact layer and the waterproof barrier layer; and a sealing pull strip having an anchoring end and a pull tab end, the pull strip being removably adhered to the top side of the barrier layer along the barrier layer cleavage to maintain the first half of the barrier layer in a position adjacent to the second half of the barrier layer, the pull strip positioned to underlie the absorbency layer, wherein the pull strip is a sufficient length to traverse substantially the length of the barrier layer along the barrier layer cleavage and maintain a fold in the pull strip to double back across the length of the barrier layer, wherein the pull tab end of the pull strip extends beyond a first edge of the barrier layer, the pull strip being for the purpose of holding the barrier layer cleavage together until the pull strip is pulled away from the barrier layer to disengage the first half of the barrier layer from the second half of the barrier layer.

3. The method of claim 2, wherein each of the plurality of pad assemblies further comprises at least one handle tab attached to the bottom side of the barrier layer, the handle tab protruding past a second edge of the barrier layer substantially opposite the first edge of the barrier layer, the handle tab providing a handle for a user to hold for stabilization while the pull strip tab end is being pulled.

4. The method of claim 2, further comprising the step of holding a handle tab to assist in stabilizing the uppermost pad assembly while the pull string is being pulled from the uppermost pad assembly.

5. The method of claim 2, wherein each of the plurality of pad assemblies comprises one of a substantially rectangular, circular triangular, oval, square and polygonal shape.

6. The method of claim 2, wherein, in each of the plurality of pad assemblies, the contact layer is bonded to the absorbency layer.

7. The method of claim 2, wherein, in each of the plurality of pad assemblies, the barrier layer is bonded to the absorbency layer.

8. The method of claim 2, wherein, in each of the plurality of pad assemblies, the contact layer is selected from the material group consisting of acrylics, high density polyethylene, low density polyethylene, polyester, polyolefins, polyurethanes, polyurethane-polyurea copolymers, rayons, spunbond polypropylene, and blends of these materials.

9. The method of claim 2, wherein, in each of the plurality of pad assemblies, the contact layer comprises material containing silver nano-particulates.

10. The method of claim 2, wherein, in each of the plurality of pad assemblies, the absorbency layer is selected from the material group consisting of acrylics, bamboo, cellulose materials, cotton, high density polyethylene, low density polyethylene, polyester, polyolefins, polyurethanes, polyurethane-polyurea copolymers, rayons, superabsorbent polymers, wools, and blends of these materials.

11. The method of claim 2, wherein, in each of the plurality of pad assemblies, the waterproof barrier layer is selected from the material group consisting of acrylics, spun bond high density polyethylene, high density polyethylene, layered low density polyethylene film, low density polyethylene, polyester, polyolefins, polyurethanes, polyurethane-polyurea copolymers, polytetrafluoroethylene, spunbond polypropylene, and blends of these materials.

* * * * *